US007858122B2

(12) United States Patent
Kshirsagar et al.

(10) Patent No.: US 7,858,122 B2
(45) Date of Patent: Dec. 28, 2010

(54) EXTENDED RELEASE FORMULATION OF LEVETIRACETAM

(75) Inventors: Rajesh Kshirsagar, Vadodara (IN); Mayank Joshi, Vadodara (IN); Yogesh Raichandani, Vododara (IN)

(73) Assignee: UCB Pharma S.A., Brussels (BE)

( * ) Notice: Subject to any disclaimer, the term of this patent is extended or adjusted under 35 U.S.C. 154(b) by 1113 days.

(21) Appl. No.: 11/215,947

(22) Filed: Aug. 31, 2005

(65) Prior Publication Data

US 2006/0165796 A1 Jul. 27, 2006

(30) Foreign Application Priority Data

Jan. 27, 2005 (IN) .......................... 81/MUM/2005

(51) Int. Cl.
*A01N 43/36* (2006.01)
*A61K 31/40* (2006.01)
*A61K 9/22* (2006.01)

(52) U.S. Cl. ........................ 424/468; 514/423
(58) Field of Classification Search ................. 514/423; 424/468
See application file for complete search history.

(56) References Cited

U.S. PATENT DOCUMENTS

| | | | |
|---|---|---|---|
| 4,389,393 A * | 6/1983 | Schor et al. ................. | 424/469 |
| 4,543,370 A | 9/1985 | Porter et al. | |
| 4,803,080 A | 2/1989 | Benedikt et al. | |
| 4,837,223 A | 6/1989 | Gobert et al. | |
| 4,943,639 A | 7/1990 | Gobert et al. | |
| 5,314,697 A | 5/1994 | Kwan et al. | |
| 5,378,474 A | 1/1995 | Morella et al. | |
| 5,605,889 A | 2/1997 | Curatolo et al. | |
| 6,107,492 A | 8/2000 | Futagawa et al. | |

(Continued)

FOREIGN PATENT DOCUMENTS

WO    WO 01/151033    7/2001

(Continued)

OTHER PUBLICATIONS

Aulton, Design of peroral modified-release drug delivery systems, Pharmaceuticals, the science of dosage form design, $2^{nd}$ ed, p. 295.

(Continued)

*Primary Examiner*—Frederick Krass
*Assistant Examiner*—Benjamin Packard
(74) *Attorney, Agent, or Firm*—Hoxie & Associates LLC

(57) ABSTRACT

An extended release pharmaceutical composition of Levetiracetam with once a day dosage regime and the process of preparing it. The extended release tablet of Levetiracetam is with the core comprising of Levetiracetam and water dispersible rate controlling polymer, and the tablet core is optionally functional coated comprising a combination of water non-dispersible and/or water dispersible polymer. It provides extended therapeutically effective plasma levels over a twenty four hour period with diminished incidences of neuropsychiatric adverse events by eliminating the troughs and peaks of drug concentration in a patients blood plasma, which comprises administering orally to a patient in need thereof, an extended release tablet that provides a peak blood plasma level of Levetiracetam in from about eight to about Sixteen hours. The core is prepared by Wet granulation, Dry granulation or Direct compression and optionally the tablet core is coated either in an coating pan or in and Fluidized bed system.

5 Claims, 2 Drawing Sheets

U.S. PATENT DOCUMENTS

| | | | |
|---|---|---|---|
| 6,274,171 | B1 | 8/2001 | Sherman et al. |
| 2004/0062805 | A1* | 4/2004 | Vandecruys et al. ......... 424/471 |
| 2004/0185097 | A1 | 9/2004 | Kannan et al. |
| 2004/0259933 | A1* | 12/2004 | Dolitzky et al. ............. 514/424 |
| 2005/0202088 | A1 | 9/2005 | Hanshermann et al. |
| 2006/0008527 | A1 | 1/2006 | Lagoviyer et al. |
| 2006/0269605 | A1 | 11/2006 | Lizio et al. |
| 2007/0105912 | A1 | 5/2007 | Holm et al. |
| 2007/0196481 | A1 | 8/2007 | Amidon et al. |

FOREIGN PATENT DOCUMENTS

| | | |
|---|---|---|
| WO | WO 03/039519 | 5/2003 |
| WO | WO 03/101428 | 12/2003 |
| WO | WO 2004/105682 | 12/2004 |

OTHER PUBLICATIONS

Collins et al., Extended release formulations of anticonvulsant medications, CNS Drugs, 2000, vol. 14, No. 3, p. 203-212.

De Smedt et al., Levetiracetam: Part II, the clinical profile of a novel anticonvulsant drug, CNS Drug Reviews, 2007, vol. 13, No. 1, p. 57-78.

Edwards et al., Levetiracetam levels in human cerebrospinal fluid, AAAN Enterprises, Inc., 2004, vol. 62 (7), supplement S5, p. A118.

Epstein et al., Prolonged neurophysiologic effects of levetiracetam after oral administration in humans, Epilepsia, 2008, 49 (7), p. 1169-1173.

Harden, Safety profile of levetiracetam, Epilepsia, 2001, 42 (suppl. 4), p. 36-39.

Patsalos, Clinical Pharmacokinetics of levetiracetam, Clin.Pharm, 2004, 43(11), p. 707-724.

Patsalos et al., *In Situ* metabolism of levetiracetam in blook of patients with epilepsy, Epilepsia, 2006, 47(11), p. 1818-1821.

Radtke, Pharmacokinetics of levetiracetam, Epilepsia, 2001, 42 (suppl. 4), p. 24-27.

Dow Product Brochure, Sep. 2006.

Keppra Prescribing Information, 2008.

Tong et al., A microdialysis study of the novel antiepileptic drug levetiracetam: extracellular pharmacokinetics and effect on taurine in rat brain, British Journal of Pharmacology, 2001, 133, p. 867-874.

* cited by examiner

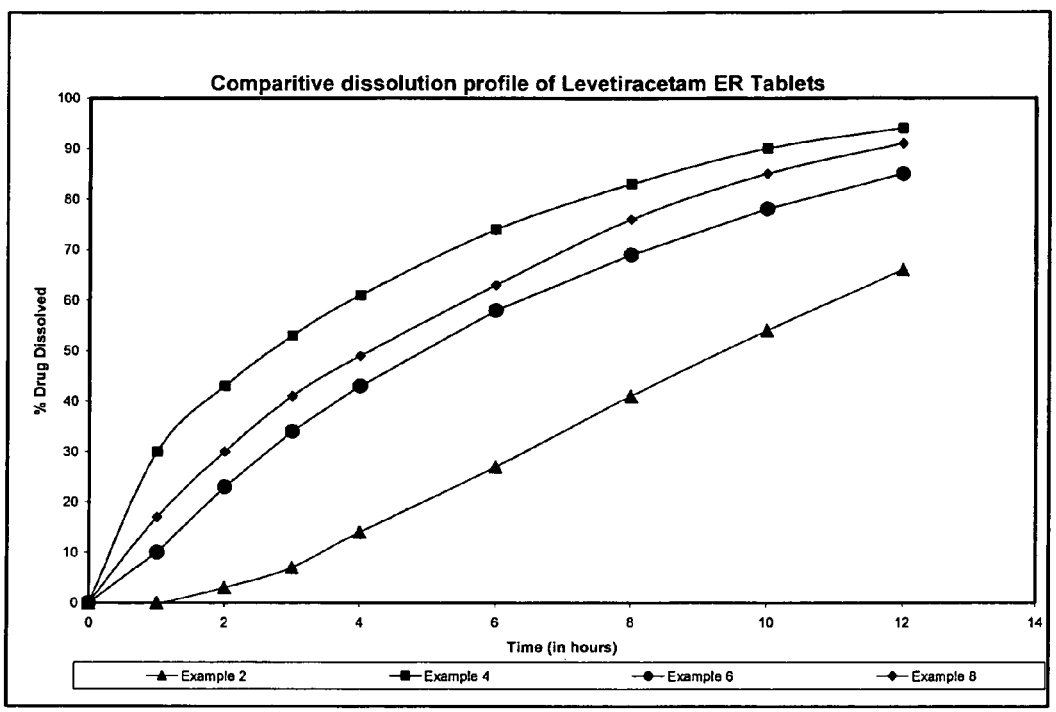
Figure: 1

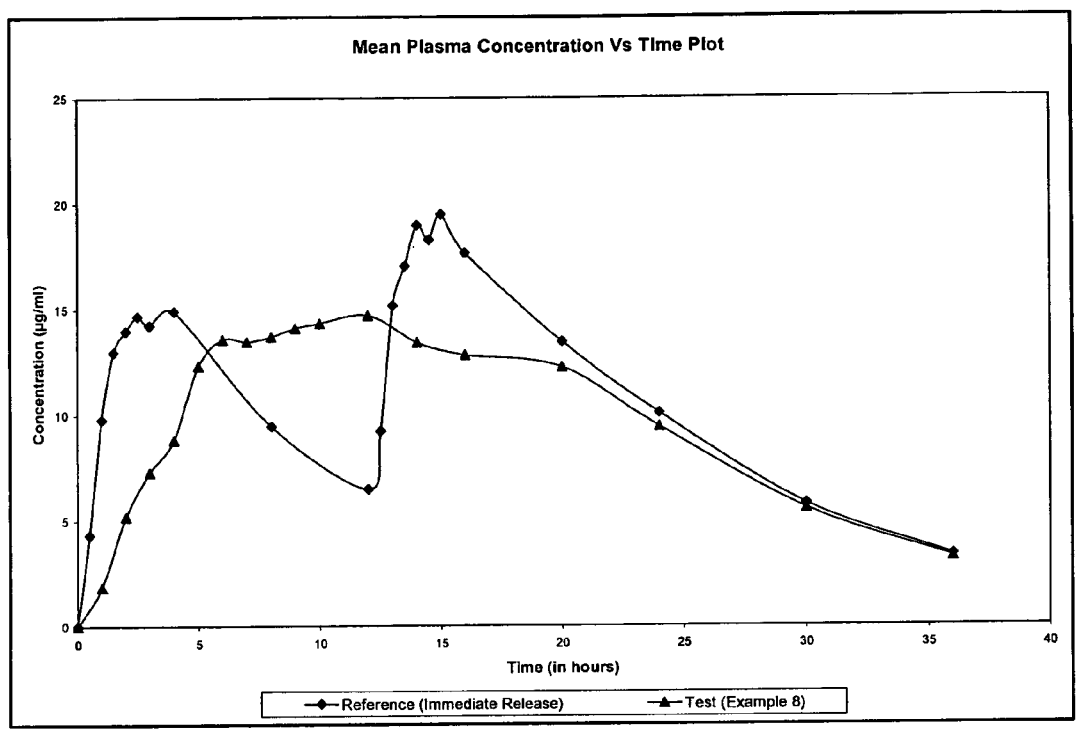
Figure: 2

EXTENDED RELEASE FORMULATION OF LEVETIRACETAM

FIELD OF INVENTION

This invention relates to an extended release pharmaceutical composition of Levetiracetam with once a day dosage regime and the process of preparing it.

BACKGROUND AND PRIOR ART

The use of high viscosity grade hydrophilic and the hydrophobic polymers to produce extended or controlled release pharmaceutical composition is known in the art. For extending the release, the tablet comprising the drug also comprises of high viscosity grade hydrophilic polymer. If required the tablets are coated with hydrophobic polymer and pore forming agent. As soon as the solid dosage form comes in contact with the surrounding media, pores are formed and the drug is diffused through these pores. The media enters the tablet core and results into the hydration of the polymer which also control the release of the drug. Control of the rate of release benefits therapy by producing constant blood plasma levels of the active ingredient and by decreasing the frequency of administration, thereby improving the patient compliance to the dosage regimen. The present invention provides a pharmaceutical composition of extended release tablets of Levetiracetam suitable for once daily administration to human subjects.

Levetiracetam is chemically named as (−)-(S)-☐-ethyl-2-oxo-1-pyrrolidine acetamide with molecular formula C8H14N2O2 and molecular weight 170.21. Levetiracetam is white to off white crystalline powder and has aqueous solubility of 104 gm/ml. It is freely soluble in chloroform (65.3 g/100 mL) and in methanol (53.6 g/100 mL), soluble in ethanol (16.5 g/100 mL), sparingly soluble in acetonitrile (5.7 g/100 mL) and practically insoluble in n-hexane. Levetiracetam is described in the U.S. Pat. Nos. 4,837,223, 4,943,639 and 6,107,492.

Levetiracetam is indicated as adjunctive therapy in the treatment of partial onset seizures in adults with epilepsy. The precise mechanism(s) by which Levetiracetam exerts its antiepileptic effect is unknown and does not appear to derive from any interaction with known mechanisms involved in inhibitory and excitatory neurotransmission. Levetiracetam is rapidly absorbed with the oral bioavailability of 100%. Food does not affect the extent of absorption of Levetiracetam but it decreases Cmax by 20% and delays Tmax by 1.5 hours. The pharmacokinetics of Levetiracetam are linear over a dose range of 500-5000 mg, with steady state kinetics being achieved 2 days after multiple twice daily dosing. It is less than 10% bound to plasma proteins. Levetiracetam has has plasma elimination half life of 7±1 hr with the volume of distribution of 0.6 L/Kg. The total body clearance is 0.9 ml/min/kg and the renal clearance is 0.6 ml/min/kg. Its elimination is correlated with creatinine clearance. There is no age, gender, race or circadian effect.

Presently Levetiracetam is administered to adults as conventional immediate release tablets. The current dosing regimen includes twice daily administration. Levetiracetam is available as an immediate release and is approved for sale in various countries including the United States of America under the brand name KEPPRA™ (UCB Pharma.). KEPPRA™ is available in 250,500 and 750 mg strengths as the immediate release tablet formulation.

In the Biopharmaceutics Classification System, it belongs to Class I since it is highly soluble (1.04 g/ml), highly permeable (F>90%) and >85% of the tablet amount released in 15 minutes in three different pH media. Clinically, it does not belong to narrow therapeutic class because it has a relatively low order of toxicity and a relatively high therapeutic index.

The twice daily dosing regimen for immediate-release Levetiracetam tablets is well tolerated with few incidences of neuropsychiatric adverse events like, somnolence, fatigue, coordination difficulties and behavioral abnormalities. The adverse effect are proportionate to the drug plasma level and therefore for improving the therapeutic efficacy, reducing incidences of adverse events and enhancing patient compliance an extended release once-daily regimen is explored in the present invention.

WO/01/51033 provides for a Solid pharmaceutical compound that can be administered orally, permitting controlled release of at least one active substance which can be Levetiracetam consisting of a homogeneous mixture comprising active substance, at least one matrix excipient between 5 and 95% by weight in relation to total weight of the compound, selected among the inert matrices, the hydrophilic, or lipid matrices, mixtures of inert and lipidic matrices mixture of hydrophilic and inert matrices; at least one entero-soluble polymer between 2 and 50% by weight in relation to the total weight of the compound and at least one alkalinizing agent soluble in a aqueous phase under conditions of physiological pH, of at least 0.5 to 50% by weight in relation to the total weight of the compound.

WO/03/101428 provides for a method for the manufacture of a pharmaceutical compound with retarded release of the active principle, which can be Levetiracetam. A mixture of active substance and the polymer that provides the retarded release are compressed by putting them through two rollers, that have a temperature of more than 40° C. and compaction force is exerted on it of more than 15 to 40 kN/cm roller width. The compressed mixture is powdered to the desired particle size and if required the process is repeated.

OBJECTIVES OF INVENTION

The object of the present invention is to provide an extended release pharmaceutical composition of Levetiracetam, which upon ingestion results in blood plasma levels having plateau effect, for an extended period of time Another object of the present invention is to produce a pharmaceutical composition which releases Levetiracetam in predetermined manner.

Yet another object of the present invention is to provide extended release pharmaceutical composition of Levetiracetam for once daily dosage regimen.

SUMMARY OF THE INVENTION

The present invention relates to the process of preparing an extended release pharmaceutical composition of Levetiracetam which comprises Levetiracetam, optionally a binder, hydrophilic rate controlling polymer and conventional pharmaceutically acceptable excipients, the blend is compressed into a tablet and the formed tablet is further coated with a functional coating comprising of an hydrophobic rate controlling polymer. The functional coating optionally comprises of a channeling agent which can be a hydrophilic polymer or a water soluble substance. The composition may be further coated with a polymer based non functional coating. The components are selected in such a way to give extended release of Levetiracetam in a predetermined manner.

Preferably, the present invention relates to the extended release formulation which comprises from about 30% w/w to about 85% w/w of Levetiracetam, from about 1% w/w to about 50% w/w of hydrophilic polymer and optionally from about 1% w/w to about 10% w/w binder. All this weights are in relation to the weight of the core tablets. The tablet is further functional coated with a hydrophobic polymer, which comprise of about 2% w/w to about 15% w/w of the weight of core tablet. The coating optionally comprises channeling agent from about 10% w/w to about 60% w/w of the total weight of the coating layer. Further the coated tablet is given a nonfunctional coating which comprises about 1% w/w to 3% w/w of the total weight of the composition.

More preferably the present invention relates to the extended release formulation which comprises from about 50% w/w to about 75% w/w of Levetiracetam, from about 0.5% to about 5% Polyvinyl pyrrolidone, from about 20% w/w to about 45% w/w Hydroxypropyl Methylcellulose. The functional coating on the tablets comprises of from about 2% w/w to about 5% w/w of the total weight of the composition. The coating comprises from about 50% w/w to about 80% w/w ethyl cellulose as functional polymer and from about 15% w/w to about 35% w/w Hydroxypropyl Methylcellulose, as a channeling agent.

According to the present invention, the extended release formulation is prepared by compression of a matrix tablet followed by functional coating, the said method comprising steps of:
i. Blending Levetiracetam or its granules prepared by dry or wet granulation with the rate controlling polymer.
ii. Lubricating the blended mixture and compressing into tablets of appropriate shape.
iii. Coating the tablets with an aqueous dispersion of water insoluble and water soluble polymer.
iv. Coating the tablets with an aqueous dispersion of the nonfunctional coating polymer.

BRIEF DESCRIPTION OF DRAWINGS

FIG. 1 is a plot showing the drug release profile of Levetiracetam from four different compositions of the drug in matrices using USP I, 100 rpm and at 37° C.

FIG. 2 is a plot showing the comparative plasma level profile of Levetiracetam under Fed dosing in Healthy Human volunteers.

DETAILED DESCRIPTION OF THE INVENTION

In an embodiment of the present invention, the extended release tablet comprises of active ingredient and water soluble rate controlling polymer and optionally conventional excipients including a binder. These tablets are coated with a combination of water insoluble polymer. The coating optionally includes a water soluble polymer or substance as a channeling agent. The functional coated tablets are further coated with water soluble polymer as non functional coat.

According to the embodiment of the present invention the active ingredient is used as such, inclusive or exclusive of the binder, if the crystal morphology is favoring direct compression. However, if the particles are not favoring direct compression and granulation is required than it is carried out either as 'dry granulation' or as 'wet granulation'. The dry granulation process involves the mixing of drug with the binder or directly with the rate controlling hydrophilic polymer or both, followed by slug formation on tablet press or using the roll compactors. The process of wet granulation includes aqueous or non aqueous granulation. The wet granulation process comprises the admixing of the active ingredient with 'diluent' or mixture of 'diluent' and rate controlling hydrophilic polymer, and granulation of the blend with the binder mass to form the wet mass followed by drying and sizing. The binder may optionally be admixed with the dry blend and granulation performed with aqueous or non aqueous solvent. The solvent for the non aqueous granulation is selected from ethanol, isopropyl alcohol and dichloromethane.

According to the present invention, the pharmaceutical composition contains Levetiracetam as an active ingredient. The Levetiracetam may be present in an amount from about 40% to about 80%, more preferably form about 50% to about 75% by weight of extended release composition.

In the preferred embodiment of the present invention Levetiracetam is granulated using aqueous granulation with a binder solution. The binder used is essentially important to impart compressibility, flow property and strength/hardness. The binder can be selected from Polyvinyl pyrrolidone, Hydroxypropyl cellulose, Hydroxypropyl Methylcellulose (low viscosity grade), methyl cellulose, starch, pregelatinized starch, modified corn starch, polyacryl amide, poly-N-vinyl amide, sodium carboxymethyl cellulose, polyethylene glycol, gelatin, polyethylene oxide, poly propylene glycol, tragacanth, alginic acid, combinations there of and other materials known to one of ordinary skill in the art. The binder may be present in an amount from about 0.01% to about 10%, preferably from about 0.5% to about 5% by weight of the extended release composition.

According to the embodiment of the present invention the active granules are blended with hydrophilic rate controlling polymer of high viscosity grade as a part of the matrix system. The high viscosity grade is the one which provide viscosity greater than 15 cps in a 2% w/w solution. The hydrophilic rate controlling polymer in the matrix system includes Hydroxyethyl cellulose, Hydroxypropyl cellulose, sodium alginate, carbomer (Carbopol™), sodium carboxymethyl cellulose, xanthan gum, guar gum, locust bean gum, poly vinyl acetate, polyvinyl alcohol and Hydroxypropyl Methylcellulose (high viscosity grade). The matrix forming polymer comprises from about 1% to about 50%, preferably from about 20% to about 40% by weight of the coated extended release composition.

In addition to the above ingredients the extended release tablets as described here also contains the lubricant, anti adherent and a glidant. Antiadherents include, by way of example and without limitation, magnesium stearate, talc, calcium stearate, glyceryl behenate, Polyethylene glycols, hydrogenated vegetable oil, mineral oil, stearic acid and other materials known to one of ordinary skill in the art. Glidants include cornstarch, talc, calcium silicate, magnesium silicate, colloidal silicon dioxide, silicon hydrogel and other materials known to one of ordinary skill in the art. Lubricants include, by way of example and without limitation, calcium stearate, magnesium stearate, sodium stearyl fumerate, glyceryl palmitostearate, glyceryl stearate, mineral oil, stearic acid, and zinc stearate and other materials known to one of ordinary skill in the art. The glidants, lubricants and anti adherents are individually present in the range from about 0.01% to about 5% w/w of the coated tablets. Preferably the glidants, anti adherents and lubricants are present in the range from about 0.5% to about 4% weight of the coated tablets, either alone or in combination.

The formed extended release tablets are coated with a hydrophobic rate controlling polymeric coat and the rate controlling polymeric coat is composed of hydrophobic polymer, hydrophobic or hydrophilic plasticizer and/hydrophilic pore forming polymer (channeling agent). The hydrophobic film forming polymer is selected from the group consisting of cellulose ether such as ethyl cellulose, cellulose acetate, polyvinyl acetate, methacrylic acid esters neutral polymer, polyvinyl alcohol-maleic anhydride copolymers and the like. Even the commercially available dispersion of film formers namely, Eudragit L-30D, Eudragit NE 30D, Aquacoat ECD-30, Surelease E-7, Eudragit RS 30D, Eudragit RL 30D, etc. may be used for the purpose of providing rate controlling coat. The hydrophilic pore forming polymer in the rate controlling coat is said to be selected from copolyvidone, Polyvinyl pyrrolidone, polyethylene glycols, Hydroxyethyl cellulose, Hydroxypropyl Methylcellulose (low viscosity grade). In the current embodiment, the water insoluble polymer is present in an amount from 40% to about 90%, preferably from about 50% to about 80% by weight of the functional coating layer of extended release composition. The water soluble pore forming polymer is present in an amount from about 10% to about 60%, preferably from about 15% to about 35% by weight of the coating layer. Additionally the coating dispersion may also comprise of plasticizer to modify the properties and characteristics of the polymers used on the coat of the compressed tablets. Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl, ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. Also the combination of the plasticizers can be used in the present formulation. The composition in the present embodiment preferably comprises 1.0 to 10.0% of hydrophobic polymer per weight of the coated tablets; optionally up to 5% per weight of hydrophilic pore forming polymer of the coated tablets and optionally up to 2% of plasticizer per weight of the coated tablets.

According to the present invention, the non-functional coating is selected from the group of ready to form dispersion such as OPADRY. The OPADRY comprises of the hydrophilic (low viscosity grade) film forming polymer, suitable colorant and the opacifying agent. Opacifying agent include by titanium dioxide and other materials known to one of ordinary skill in the art. Colorant include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The following examples should not be considered exhaustive, but merely illustrative of only a few of the many embodiments contemplated by the present invention.

EXAMPLES 1-2

TABLE 1

| | Composition | | |
|---|---|---|---|
| Sr. No. | Ingredient | Weight in mgs Ex. 1 | Ex. 2 |
| 1 | Levetiracetam | 500.00 | 500.00 |
| 2 | Povidone | 05.00 | 05.00 |
| 3 | Purified water | q.s. | q.s. |
| 4 | Hydroxypropyl Methylcellulose (HV) | 300.00 | 300.00 |
| 5 | Magnesium Stearate | 10.00 | 10.00 |
| 6 | Colloidal silicon dioxide | 5.00 | 5.00 |
| 7 | Aqueous dispersion of Ethyl cellulose (solid content) | — | 24.30 |
| | Total | 820 | 844.30 | q.s. means quantity sufficient.

Levetiracetam 500 mg was sifted through s. s. sieve of mesh 40 and was then granulated with aqueous Polyvinyl pyrrolidone solution and the granulated mass was dried at 50° C. The dried granules were sized through s. s. sieve of mesh 20 mesh and these granules were blended with Hydroxypropyl Methylcellulose, lubricated with magnesium stearate and colloidal silicon dioxide and the lubricated granules were compressed into tablets.

As mentioned in Table 1 the tablets of example 2 were further coated with aqueous dispersion of hydrophobic rate controlling ethyl cellulose to weight gain of 2.96% w/w of the compressed tablet. Following the functional coating the tablets were cured at 55° C. for 1 hour.

EXAMPLE 3

TABLE 2

| | Composition | |
|---|---|---|
| Sr. No. | Ingredient | Weight in mgs Ex. 3 |
| 1 | Levetiracetam | 500.00 |
| 2 | Povidone | 05.00 |
| 3 | Purified water | q.s. |
| 4 | Hydroxypropyl Methylcellulose (HV) | 300.00 |
| 5 | Magnesium Stearate | 10.00 |
| 6 | Colloidal silicon dioxide | 5.00 |
| 7 | Aqueous dispersion of Ethyl cellulose (solid content) | 35.82 |
| 8 | Opadry | 42.98 |
| | Total | 898.80 | q.s. means quantity sufficient.

Levetiracetam 500 mg was sifted through s. s. sieve of mesh 40 and was then granulated with aqueous Polyvinyl pyrrolidone solution and the granulated mass was dried at 50° C. The dried granules were sized through s. s. sieve mesh 20 mesh and these granules are blended with Hydroxypropyl Methylcellulose, lubricated with magnesium stearate and colloidal silicon dioxide and lubricated granules were compressed into tablets. The compressed tablets were coated with the mixture of aqueous dispersion of ethyl cellulose and Opadry to a weight gain of 9.60% w/w of the compressed tablets. Following the functional coating the tablets were cured at 55° C. for 1 hour.

EXAMPLE 4

TABLE 3

| Sr. No. | Ingredient | Weight in mgs Ex. 4 |
|---|---|---|
| 1 | Levetiracetam | 500.00 |
| 2 | Povidone | 10.00 |
| 3 | Purified water | q.s. |
| 4 | Hydroxypropyl Methylcellulose (HV) | 285.00 |
| 5 | Magnesium Stearate | 10.00 |
| 6 | Colloidal silicon dioxide | 5.00 |
| 7 | Opadry | 16.30 |
| 8 | Talc | 5.00 |
|   | Total | 831.30 | q.s. means quantity sufficient.

Levetiracetam 500 mg was sifted through s. s. sieve of mesh 40 and was then granulated with aqueous Polyvinyl pyrrolidone solution and the granulated mass was dried at 50° C. The dried granules were sized through s. s. sieve of mesh 20 mesh and these granules were blended with Hydroxypropyl Methylcellulose, lubricated with magnesium stearate, talc and colloidal silicon dioxide and lubricated granules were compressed into tablets. The compressed tablets were coated with Opadry to a weight gain of 2% w/w of the compressed tablets.

EXAMPLES 5-6

TABLE 4

| Sr. No. | Ingredient | Weight in mgs Ex. 5 | Weight in mgs Ex. 6 |
|---|---|---|---|
| 1 | Levetiracetam | 500.00 | 500.00 |
| 2 | Povidone | 10.00 | 10.00 |
| 3 | Purified water | q.s. | q.s. |
| 4 | Hydroxypropyl Methylcellulose (HV) | 285.00 | 285.00 |
| 5 | Magnesium Stearate | 10.00 | 10.00 |
| 6 | Colloidal silicon dioxide | 5.00 | 5.00 |
| 7 | Aqueous dispersion of Ethyl cellulose (solid content) | 15.28 | 30.56 |
| 8 | Opadry | 16.71 | 17.12 |
| 9 | Talc | 5.00 | 5.00 |
| 10 | Hydroxypropyl Methyl cellulose (LV) | 5.10 | 10.19 |
|   | Total | 852.09 | 872.87 | q.s. means quantity sufficient.

Levetiracetam 500 mg was sifted through s.s. sieve of mesh 40 and was then granulated with aqueous Polyvinyl pyrrolidone solution and the granulated mass was dried at 50° C. The dried granules were sized through s. s. sieve of mesh 20 mesh and these granules were blended with Hydroxypropyl Methylcellulose, lubricated with magnesium stearate, talc and colloidal silicon dioxide and the lubricated granules were compressed into tablets.

The tablets of example 5 and 6, as mentioned in the table 4, were coated with mixture of aqueous dispersion of ethyl cellulose and Hydroxypropyl Methylcellulose (LV; low viscosity) in the ratio of 75:25 (solid content). The tablets were coated to target weight gain of 2.5% w/w and 5.0% w/w of the compressed tablets for example 5 and example 6 respectively. Following the coating the tablet were cured at 65° C. for 1 hr.

The coated tablets were further coated with Opadry to a weight gain of 2% w/w of the functional coated tablet.

EXAMPLE 7

The extended release tablets of Examples 1 to Example 6 were tested for dissolution of Levetiracetam using 900 ml of pH 6.8 phosphate buffer as dissolution media at 37° C. and in 40-mesh basket (USP Type 1) at 100 rpm The dissolution profiles are recorded in Table 5.

TABLE 5

Dissolution Profile

| Time (hrs) | Percentage Levetiracetam dissolved | | | | | |
|---|---|---|---|---|---|---|
|  | Ex. 1 | Ex. 2 | Ex. 3 | Ex. 4 | Ex. 5 | Ex. 6 |
| 1 | 26 | 0 | 16 | 30 | 16 | 10 |
| 2 | 40 | 3 | 30 | 43 | 30 | 23 |
| 3 | 51 | 7 | 41 | 53 | 41 | 34 |
| 4 | 60 | 14 | 51 | 61 | 51 | 43 |
| 6 | 75 | 27 | 67 | 74 | 66 | 58 |
| 8 | 88 | 41 | 81 | 83 | 80 | 69 |
| 10 | 98 | 54 | 94 | 90 | 90 | 78 |
| 12 | 105 | 66 | 103 | 94 | 99 | 85 |

EXAMPLE 8

TABLE 6

| Sr. No. | Ingredient | Weight in mgs Ex. 8 |
|---|---|---|
| 1 | Levetiracetam | 750.00 |
| 2 | Povidone | 15.00 |
| 3 | Purified water | q.s. |
| 4 | Hydroxypropyl Methylcellulose (HV) | 316.00 |
| 5 | Magnesium Stearate | 12.00 |
| 6 | Colloidal silicon dioxide | 6.00 |
| 7 | Talc | 6.00 |
| 8 | Aqueous dispersion of Ethyl cellulose (solid content) | 16.58 |
| 9 | Opadry | 22.54 |
| 10 | Hydroxy Propyl Methyl Cellulose (LV) | 5.52 |
|   | Total | 1149.64 | q.s. means quantity sufficient.

Levetiracetam 750 mg was sifted through s. s. sieve of mesh 40 and was then granulated with aqueous Polyvinyl pyrrolidone solution and the granulated mass was dried at 50° C. The dried granules are sized through s. s. sieve of mesh 20 mesh and these granules were blended with Hydroxypropyl Methylcellulose and then lubricated with magnesium stearate, colloidal silicon dioxide and talc and the lubricated granules were compressed into tablets.

The tablets as mentioned in the table 6, were coated with mixture of aqueous dispersion of ethyl cellulose and Hydroxypropyl Methylcellulose LV in the ratio of 75:25 (solid content). The tablets were coated to target weight gain of 2.0% w/w. Following the coating the tablet were cured at 65° C. for 1 hr.

The coated tablets were further coated with Opadry to a weight gain of 2% w/w of the functional coated tablet.

EXAMPLE 9

TABLE 7

| Composition | | |
|---|---|---|
| Sr. No. | Ingredient | Weight in mgs Ex. 9 |
| 1 | Levetiracetam | 750.00 |
| 2 | Carbopol (71 G) | 330 |
| 3 | Glyceryl Behenate | 15 |
| 4 | Colloidal silicon dioxide | 5 |
| 5 | Talc | 5 |
| | Total | 1105 | q.s. means quantity sufficient.

Levetiracetam 750 mg and carbopol were sifted through s. s. sieve of mesh 30 and were blended together. The blend was lubricated with glyceryl behenate, colloidal silicon dioxide and talc and the lubricated blend was compressed into tablets.

EXAMPLE 10

TABLE 8

| Composition | | |
|---|---|---|
| Sr. No. | Ingredient | Weight in mgs Ex. 10 |
| 1 | Levetiracetam | 750.00 |
| 2 | Polyvinyl Acetate | 275 |
| 3 | Glyceryl Behenate | 15 |
| 4 | Colloidal silicon dioxide | 5 |
| 5 | Talc | 5 |
| 6 | Aqueous dispersion of Ethyl cellulose (solid content) | 15.00 |
| 7 | Opadry | 20 |
| 8 | Hydroxy Propyl Methyl Cellulose (LV) | 5 |
| | Total | 1145 | q.s. means quantity sufficient.

Levetiracetam 750 mg and Kollidon SR (Polyvinyl Acetate: Polyvinyl Pyrolidone, 8:2) were sifted through s. s sieve of mesh 30 and blended together. The blend was lubricated with glyceryl behenate, colloidal silicon dioxide and talc and the lubricated blend was compressed into tablets.

The tablets as mentioned in the table 8, were coated with mixture of aqueous dispersion of ethyl cellulose and Hydroxypropyl Methylcellulose (LV) in the ratio of 75:25 (solid content). The tablets were coated to target weight gain of 1.90% w/w of the uncoated tablets. Following coating the tablet were cured at 65° C. for 1 hr.

The functional coated tablets were further coated with Opadry to a weight gain of 1.87% w/w of the functional coated tablet.

EXAMPLE 11

TABLE 9

| Composition | | |
|---|---|---|
| Sr. No. | Ingredient | Weight in mgs Ex. 11 |
| 1 | Levetiracetam | 750.00 |
| 2 | Hydroxypropyl Methylcellulose (HV) | 350 |

TABLE 9-continued

| Composition | | |
|---|---|---|
| Sr. No. | Ingredient | Weight in mgs Ex. 11 |
| 3 | Magnesium Stearate | 12.00 |
| 4 | Colloidal silicon dioxide | 6.00 |
| 5 | Talc | 6.00 |
| 6 | Aqueous dispersion of Ethyl cellulose (solid content) | 15.00 |
| 7 | Opadry | 20 |
| 8 | Hydroxy Propyl Methyl Cellulose (LV) | 5 |
| | Total | 1164 | q.s. means quantity sufficient.

Levetiracetam 750 mg and hydroxyl propyl methyl cellulose (HV) were sifted through s. s. sieve of mesh 40 and blended together. The blend was compacted using a roll compactor (Chilsonator) to form slugs. The slugs were sized in an oscillating granulator using a s. s. sieve of mesh 20. Obtained granules were lubricated with magnesium stearate, colloidal silicon dioxide and talc. The lubricated blend was compressed into tablets.

The tablets as mentioned in the table 9 were coated with mixture of aqueous dispersion of ethyl cellulose and Hydroxypropyl Methylcellulose (LV) in the ratio of 75:25 (solid content). The tablets were coated to target weight gain of 1.78% w/w of the uncoated tablets. Following the coating the tablet were cured at 65° C. for 1 hr.

The functional coated tablets were further coated with Opadry to a weight gain of 1.75% w/w of the functional coated tablet.

EXAMPLE 12

TABLE 10

| Composition | | |
|---|---|---|
| Sr. No. | Ingredient | Weight in mgs Ex. 12 |
| 1 | Levetiracetam | 750.00 |
| 2 | Hydroxypropyl Methylcellulose (HV) | 271 |
| 3 | Hydroxypropyl Cellulose | 45.00 |
| 4 | Magnesium Stearate | 12.00 |
| 5 | Colloidal silicon dioxide | 6.00 |
| 6 | Talc | 6.00 |
| 7 | Aqueous dispersion of Ethyl cellulose (solid content) | 15.00 |
| 8 | Opadry | 20 |
| 9 | Hydroxy Propyl Methyl Cellulose (LV) | 5 |
| | Total | 1164 | q.s. means quantity sufficient.

Levetiracetam 750 mg and Hydroxylpropyl Methylcellulose (HV) were sifted through s. s. sieve of mesh 40 and blended together. The blend was granulated using nonaqueous granulation using Hydroxypropyl Cellulose as the binder. The granulated mass was dried at 45° C. The dried granules were sized through s. s. sieve of mesh 20 and the granules were lubricated with Magnesium Stearate, Talc and Colloidal Silicon dioxide. The lubricated blend was compressed into tablets.

The tablets as mentioned in the table 10 were coated with mixture of aqueous dispersion of ethyl cellulose and Hydroxypropyl Methylcellulose LV in the ratio of 75:25 (solid content). The tablets were coated to target weight gain of 1.78% w/w of the uncoated tablets. Following the coating the tablet were cured at 65° C. for 1 hr.

The coated tablets were further coated with Opadry to a weight gain of 1.75% w/w of the functional coated tablet.

EXAMPLE 13

TABLE 11

Composition

| Sr. No. | Ingredient | Weight in mgs Ex. 13 |
|---|---|---|
| 1 | Levetiracetam | 750.00 |
| 2 | Hydroxypropyl Cellulose | 45.00 |
| 3 | Hydroxyethyl cellulose | 271 |
| 4 | Magnesium Stearate | 12.00 |
| 5 | Colloidal silicon dioxide | 6.00 |
| 6 | Talc | 6.00 |
| 7 | Aqueous dispersion of Ethyl cellulose (solid content) | 15.00 |
| 8 | Opadry | 20 |
| 9 | Hydroxy Propyl Methyl Cellulose (LV) | 5 |
| | Total | 1164 | q.s. means quantity sufficient.

Levetiracetam 750 mg was sifted through s. s. sieve of mesh 40 and was then granulated with non aqueous Hydroxypropyl cellulose solution and the granulated mass was dried at 45° C. The dried granules are sized through s. s. sieve of mesh 20 and these granules were blended with Hydroxyethyl cellulose and lubricated with magnesium stearate, colloidal silicon dioxide and talc. The lubricated granules were compressed into tablets.

The tablets as mentioned in the table 11, were coated with mixture of aqueous dispersion of ethyl cellulose and Hydroxypropyl Methylcellulose (LV) in the ratio of 75:25 (solid content). The tablets were coated to target weight gain of 1.78% w/w. The coated tablet were cured at 65° C. for 1 hr.

The functional coated tablets were further coated with Opadry to a weight gain of 1.75% w/w of the functional coated tablet.

EXAMPLE 14

The extended release tablets of Examples 8 to Example 13 were tested for dissolution of Levetiracetam using 900 ml of pH 6.8 phosphate buffer as dissolution media at 37° C. and in 40-mesh basket (USP Type 1) at 100 rpm The dissolution profiles are recorded in Table 12.

TABLE 12

Dissolution Profile

Percentage Levetiracetam dissolved

| Time (hrs) | Ex. 8 | Ex. 9 | Ex. 10 | Ex. 11 | Ex. 12 | Ex. 13 |
|---|---|---|---|---|---|---|
| 1 | 17 | 23 | 9 | 18 | 6 | 6 |
| 2 | 30 | 44 | 26 | 33 | 12 | 30 |
| 3 | 41 | 59 | 45 | 45 | 22 | 48 |
| 4 | 49 | 72 | 59 | 55 | 31 | 60 |
| 6 | 63 | 91 | 78 | 72 | 49 | 82 |
| 8 | 76 | 101 | 93 | 85 | 66 | 94 |
| 10 | 85 | 99 | 98 | 95 | 79 | 99 |
| 12 | 91 | 98 | 97 | 101 | 91 | 97 |

EXAMPLE 15

An in vivo study was conducted in healthy human volunteers to assess bioavailability of Levetiracetam formulated as the extended release tablets of Example 8 by comparison with a reference treatment with immediate release Levetiracetam tablets.

Method

The study followed an open label, two-treatment, two-periods, comparative oral bioavailability study in healthy, adult, male, human subjects under fed conditions. The subjects received each of the two treatments during the course of the study, which was conducted at a single center. The subjects were given 1500 mg oral dose of Levetiracetam. In the case of the IR formulation, which was provided as Keppra® tablets, two equally divided doses of 750 mg each were given at 12 hour interval beginning in the morning. In the case of the extended release formulation of Example 8, two tablets of 750 mg were given at a time in the morning. Plasma Levetiracetam concentrations were quantified by HPLC method. Samples were not diluted prior to analysis as all sample concentrations were within the limits of quantitation. Pharmacokinetic parameters for Levetiracetam were estimated by non compartmental methods. The parameters Tmax, Cmax, $AUC_{0 \to t}$, $AUC_{0 \to \infty}$ were estimated during the studies and recorded in Table 13.

Results

Mean plasma Levetiracetam concentrations over the 36 hour assessment period are shown in FIG. 2.

TABLE 13

| Parameter | Unit | Formulation of Example 8 | Keppra tablets 750 mg |
|---|---|---|---|
| Cmax | µg/mL | 17.194 ± 4.23 | 22.23 ± 5.44 |
| Tmax | Hrs | 12-13 | 2-3 and 14-15 |
| AUC (0->t) | µg · h/mL | 345.81 ± 105.45 | 375.267 ± 76.86 |
| AUC (0->inf) | µg · h/mL | 383.855 ± 125.87 | 413.854 ± 91.50 |

We claim:

1. An extended release tablet of levetiracetam consisting of:
   from about 30% w/w to about 85% w/w of levetiracetam;
   from about 20% w/w to about 40% w/w of a water dispersible rate controlling polymer having a viscosity greater than 15 cps in a 2% w/w solution and selected from the group consisting of hydroxyethyl cellulose, hydroxypropyl cellulose, sodium alginate, carbomer, sodium carboxymethyl cellulose, xanthan gum, guar gum, locust bean gum, polyvinyl acetate, polyvinyl alcohol, hydroxypropyl methylcellulose and mixtures thereof;
   optionally a binder selected from the group consisting of polyvinyl pyrrolidone, hydroxypropyl cellulose, hydroxypropyl methylcellulose, methyl cellulose, polyacryl amide, poly-N-vinyl amide, sodium carboxymethyl cellulose, polyethylene glycol, gelatin, polyethylene oxide, poly propylene glycol, tragacanth, alginic acid, and combinations thereof;
   optionally one or more lubricants, anti adherents, or glidants, either alone or in combination; and
   optionally a non-functional coating comprising hydrophilic film forming polymer, colorant and opacifying agent,
   wherein the tablet has the following dissolution profile in USP Apparatus 1 (basket) at 100 rpm in purified water at 37° C.:

| Time (hours) | Average % levetiracetam released |
| --- | --- |
| 2 | <35 |
| 4 | 35-75 |
| 12 | >75 |

2. An extended release tablet of levetiracetam according to claim 1, wherein the tablet provides extended therapeutically effective plasma levels over a twenty four hour period and further provides a peak blood plasma level of levetiracetam in from about eight to about sixteen hours.

3. An extended release tablet of levetiracetam according to claim 1, the tablet consisting of from about 50% to 80% levetiracetam by weight, about 20% to about 40% hydroxypropyl methylcellulose, by weight, and, optionally, from about 1% to about 5% polyvinyl pyrrolidone by weight.

4. An extended release tablet of levetiracetam according to claim 1, the tablet consisting of from about 61% to 73% levetiracetam by weight, about 25% to about 35% hydroxypropyl methylcellulose, by weight, and, optionally, from about 1.1% to about 1.5% polyvinyl pyrrolidone by weight.

5. An extended release tablet of levetiracetam according to claim 1, wherein the tablet is prepared by wet granulation, dry granulation or direct compression.

* * * * *

UNITED STATES PATENT AND TRADEMARK OFFICE
CERTIFICATE OF CORRECTION

| | |
|---|---|
| PATENT NO. | : 7,858,122 B2 |
| APPLICATION NO. | : 11/215947 |
| DATED | : December 28, 2010 |
| INVENTOR(S) | : Rajesh Kshirsagar, Mayank Joshi and Yogesh Raichandani |

It is certified that error appears in the above-identified patent and that said Letters Patent is hereby corrected as shown below:

In the first line of the table in claim 1, at column 13, line 5, the number "<35" should be changed to -- ≤44 --.

Signed and Sealed this
Eighth Day of February, 2011

David J. Kappos
*Director of the United States Patent and Trademark Office*